United States Patent
Hamied et al.

(12)

(10) Patent No.: US 6,903,228 B2
(45) Date of Patent: Jun. 7, 2005

(54) PREPARATION OF PHTHALANES

(75) Inventors: Yusuf Khwaja Hamied, Mumbai (IN); Rajendra Narayaurao Kankan, Mumbai (IN); Dhanmaraj Ramachandra Rao, Maharashtra (IN)

(73) Assignee: Cipla Limited, Mumbai (IN)

( * ) Notice: Subject to any disclaimer, the term of this patent is extended or adjusted under 35 U.S.C. 154(b) by 0 days.

(21) Appl. No.: 10/471,052

(22) PCT Filed: Mar. 7, 2002

(86) PCT No.: PCT/GB02/01054
§ 371 (c)(1),
(2), (4) Date: Nov. 18, 2003

(87) PCT Pub. No.: WO02/070501
PCT Pub. Date: Sep. 12, 2002

(65) Prior Publication Data
US 2004/0092755 A1 May 13, 2004

(51) Int. Cl.$^7$ ............................................ C07D 307/87

(52) U.S. Cl. ....................................................... 549/467
(58) Field of Search ......................................... 549/467

(56) References Cited

FOREIGN PATENT DOCUMENTS

| GB | 1526331 | * | 9/1978 |
| GB | 2357762 | * | 7/2001 |
| WO | 9930548 | * | 6/1999 |
| WO | 0013648 | * | 3/2000 |
| WO | 0145483 | * | 6/2001 |

* cited by examiner

*Primary Examiner*—Bernard Dentz
(74) *Attorney, Agent, or Firm*—Stevens, Davis, Miller & Mosher, L.L.P.

(57) ABSTRACT

Citalopram and other phthalanes are made by reacting a salt of a compound of formula (II) where $R^1$ is halogen and $R^2$ is halogen, trifluoromethyl, cyano or R—CO— where R is a $C_{1-4}$ alkyl group, with cuprous cyanide.

14 Claims, No Drawings

PREPARATION OF PHTHALANES

This application is a §371 Application of International Application No. PCT/GB02/01054, filed on Mar. 7, 2002, claiming the priority of Great Britain Application No. 0105627.4, filed Mar. 7, 2001, the entire disclosures of which are incorporated herein by reference in their entireties.

This invention relates to a process for the preparation of certain phthalanes, particularly but not exclusively citalopram.

The antidepressant drug citalopram, 1-[3-(dimethylamino)propyl]-1-(4-fluorophenyl)-1,3-dihydro-5-isobenzofurancarbonitrile, has the formula:

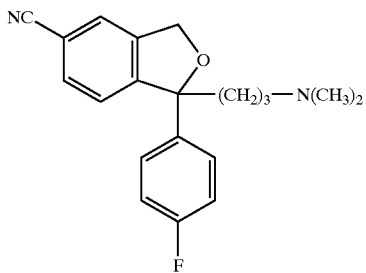

I

GB 1526331 describes citalopram and other closely similar phthalanes of formula:

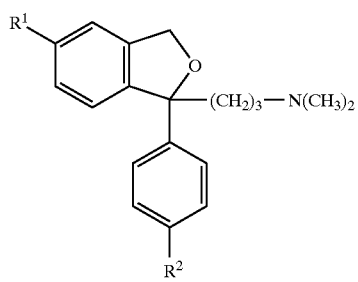

II wherein $R^1$ and $R^2$ each represents halogen, a trifluoromethyl group, a cyano group or R—CO— wherein R is an alkyl radical with from 1 to 4 carbon atoms, and acid addition salts thereof with pharmaceutically acceptable acids.

GB 1526331 describes a number of processes for making citalopram, among which is a process in which a compound of formula II in which $R^1$ is bromine and $R^2$ is fluorine, is reacted with cuprous cyanide in an inert organic solvent to obtain a compound of formula II in which $R^1$ is a cyano group, i.e. to obtain citalopram. This process is particularly described in Example 3 of GB 1526331 where the yellow oil 1-(4'-fluorophenyl)-5-bromophthalane (free base) and cuprous cyanide are refluxed in dimethyl formamide. Dimethyl formamide dissolves the bromophthalane. The citalopram so formed is crystallised out by pouring the reaction mixture into an aqueous solution of sodium cyanide.

We have investigated this process and have found that it is difficult to carry out and generally gives only a low yield. We have tried the same process but without any solvent, and whilst the reaction conversion is good, it is very difficult to isolate pure white citalopram product We have now found a way in which these difficulties can be reduced or overcome.

According to one aspect of the present invention, there is provided a process for the preparation of a phthalane of formula II in which $R^1$ is cyano and $R^2$ is as defined for formula II above, wherein a salt of a compound of formula II in which $R^1$ is halogen, is reacted with cuprous cyanide.

The process is especially useful for making citalopram in which case $R^1$ in the compound of formula II is initially bromine, chlorine or iodine, and $R^2$ is fluorine. Other phthalanes can also be made.

In the process of the invention, we prefer to use the oxalate salt, but other salts can equally be used. For example, the fumarate, acetate, maleate, mesylate, citrate, lactate, tartrate, besylate, tosylate, mandelate, benzoate, salicylate and other organic acid salts.

According to a further preferred feature of the invention, the salt is reacted with the cuprous cyanide as a suspension in an organic liquid. There are many possible such liquids, as will be clear to those skilled in the art. We prefer to use diglyme but other possible organic liquids include sulfolane, dimethylsulfoxide, N-methyl pyrrolidone, tetraglyme, ethylene glycol.

The reaction is effected under heat over a period of time. The exact conditions will depend on the organic liquid and, to a lesser extent, the salt used. The reaction is preferably conducted under an inert atmosphere, e.g. nitrogen. By way of example, we have found that in the case of the oxalate salt and using diglyme as the organic liquid, the suspension is preferably heated at 150–155° C. for about three hours. More generally, the time of heating will be from 1 to 5 hours at or below the reflux temperature of the organic liquid.

At the end of the reaction, citalopram is recovered from the reaction mixture by any suitable means. We have found that washing the organic liquid with an aqueous base and then extracting the citalopram into an aqueous acid solution is satisfactory. Upon neutralisation of the acid solution, the citalopram precipitates out and can be recrystallised as desired. Since citalopram is normally used in the form of its hydrobromide salt, conversion thereto is preferably effected in the usual way.

In the above recovery procedure, we prefer to use an aqueous solution of ethylene diamine as the base, but other bases can be used such as ammonia, monomethylamine, dimethylamine, other amines, and alkali metal hydroxides. The preferred aqueous acid solution is an organic acid solution. We prefer to use acetic acid but other acids can be used such as hydrochloric acid, sulphuric acid, phosphoric acid, formic acid and other organic and mineral acids. In order that the invention may be more fully understood, the following Example is given by way of illustration only.

EXAMPLE

Bromophthalane oxalate 100 g and cuprous cyanide 35 g are suspended in diglyme 500 ml and heated under a blanket of nitrogen to a temperature of 150–155° C. and maintained for 3 hours. The reaction mass is then cooled to 50° C. and 100 ml of a 50% aqueous solution of ethylene diamine is added. The lower aqueous layer is drained off. The organic layer is diluted with toluene 500 ml and further washed with ethylene diamine solution followed by 5% EDTA solution. The product is extracted into 10% solution of acetic acid 150 ml. Under vigorous stirring, 25% aqueous ammonia solution is then introduced into the acetic acid extract to ensure complete neutralization of the acid. The product which precipitates out is filtered. The crude product is then crystallized from n-hexane. The purified citalopram base is then taken in ethyl acetate or isopropyl alcohol, water and aqueous hydrobromic acid is added. The product is filtered and dried in a vacuum oven to obtain 35 g of citalopram hydrobromide.

What is claimed is:

1. A process for the preparation of a phthalane of formula:

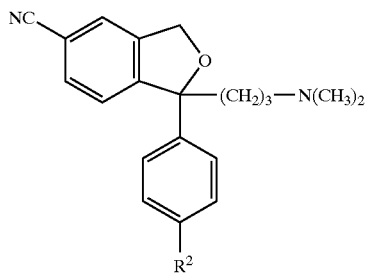

wherein $R^2$ is halogen, trifluoromethyl, cyano or R—CO— where R is an alkyl radical having from 1 to 4 carbon atoms, and acid addition salts thereof, which comprises reacting a salt of a compound of formula:

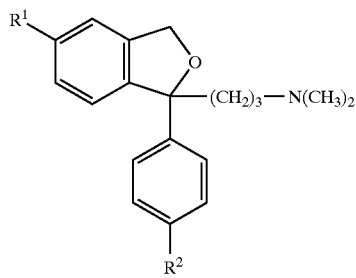

in which $R^1$ is halogen and $R^2$ is as defined above, with cuprous cyanide.

2. A process according to claim 1, wherein $R^2$ is fluorine.

3. A process according to claim 1, wherein said salt is an organic acid salt.

4. A process according to claim 3, wherein the salt of formula II is the oxalate.

5. A process according to claim 3, wherein the salt of formula II is the fumarate, acetate, maleate, mesylate, citrate, lactate, tartrate, besylate, tosylate, madelate, benzoate or salicylate.

6. A process according to claim 1, wherein the salt of formula II is reacted with the cuprous cyanide in an organic liquid.

7. A process according to claim 6, wherein the organic liquid is diglyme.

8. A process according to claim 6, wherein the organic liquid is sulfolane, dimethylsulfoxide, N-methyl pyrrolidone, tetraglyme or ethylene glycol.

9. A process according to claim 1, wherein the reaction is conducted under heating in an inert atmosphere.

10. A process according to claim 1, wherein at the end of the reaction, the reaction mixture is washed with an aqueous base, and the phthalane is extracted from the wash liquid into an aqueous acid solution.

11. A process according to claim 10, wherein the base is ammonia, an amine, or an alkali metal hydroxide, and the acid is an organic acid.

12. A process according to claim 9, wherein the aqueous acid solution extract is neutralized to precipitate the phthalane.

13. A process according to claim 1, wherein the phthalane of formula III is citalopram.

14. A process according to claim 1, wherein the phthalane of formula III is converted to a salt thereof.

* * * * *